US00PP37241P2

(12) United States Plant Patent
Flanders

(10) Patent No.: US PP37,241 P2
(45) Date of Patent: Feb. 3, 2026

(54) ***CORNUS* PLANT NAMED 'Botfire'**

(50) Latin Name: *Cornus kousa*
Varietal Denomination: Botfire

(71) Applicant: Bobby F. Flanders, McMinnville, TN (US)

(72) Inventor: Bobby F. Flanders, McMinnville, TN (US)

(73) Assignee: BOTANICO, INC., Mcminnville, TN (US)

( * ) Notice: Subject to any disclaimer, the term of this patent is extended or adjusted under 35 U.S.C. 154(b) by 0 days.

(21) Appl. No.: 19/037,195

(22) Filed: Jan. 25, 2025

(51) Int. Cl.
*A01H 5/00* (2018.01)
*A01H 6/00* (2018.01)

(52) U.S. Cl.
USPC ..... Plt./220

(58) Field of Classification Search
USPC ..... Plt./220
See application file for complete search history.

*Primary Examiner* — Shubo Zhou
*Assistant Examiner* — Zachariah Allan Kay
(74) *Attorney, Agent, or Firm* — Penny J. Aguirre

(57) ABSTRACT

A new cultivar of *Cornus* plant named 'Botfire' that is characterized by its foliage that is tinged red to bronze with the color persistent throughout fall, its flowers with dark pink to red colored flower bracts, its sturdy trunk, and its viability after chip budding onto *Cornus kousa* rootstock.

3 Drawing Sheets

Botanical classification: *Cornus kousa.*
Variety denomination: 'Botfire'.

BACKGROUND OF THE INVENTION

The present invention relates to a new and distinct cultivar of *Cornus kousa* and will be referred to hereafter by its cultivar name, 'Botfire'. 'Botfire' is a new cultivar of dogwood, a shrub grown for use as an ornamental landscape plant.

The Inventor discovered the new cultivar as a chance seedling growing in a production field at his nursery in McMinnville, Tennessee in July of 2017. The cultivated nursery production field contained unnamed and unpatented plants of *Cornus kousa.*

Asexual propagation of the new cultivar was first accomplished by the Inventor using chip budding onto *Cornus kousa* rootstock (not patented) in summer of 2018 in McMinnville, Tennessee. Asexual propagation of the new cultivar by chip budding onto *Cornus kousa* rootstock (not patented) and T budding has been determined that the characteristics are stable and are reproduced true to type in successive generations.

SUMMARY OF THE INVENTION

The following traits have been repeatedly observed and represent the characteristics of the new cultivar. These attributes in combination distinguish 'Botfire' as a unique cultivar of *Cornus.*

1. 'Botfire' exhibits foliage that is tinged red to bronze with the color persistent throughout fall.
2. 'Botfire' exhibits flowers with dark pink to red colored flower bracts.
3. 'Botfire' exhibits a sturdy trunk.
4. 'Botfire' exhibits viability after chip budding onto *Cornus kousa* rootstock.

The typical plants of *Cornus kousa* growing in the field of discovery differ from 'Botfire' in having flowers with white colored bracts and in having green leaves. 'Botfire' can be most closely compared to the *Cornus* cultivars 'Rutpink' (U.S. Plant Pat. No. 28,311) and 'Satomi' (not patented). 'Rutpink' is similar to 'Botfire' in having flowers with dark pink flower bracts. 'Rutpink' differs from 'Botfire' in being a hybrid with *Cornus florida* and typically shows union bud separation when budded onto rootstock and in having a weaker and thinner trunk at a young age (requiring staking) and a tendency for leaf curl during the hot temperature in summer and fall. 'Satomi' differs from 'Botfire' in having flowers with flower bracts that are white and become flushed with rose pink as they age and in in having foliage that is not tinged red until later in fall.

BRIEF DESCRIPTION OF THE DRA WINGS

The accompanying color photographs illustrate the overall appearance and distinct characteristics of the new *Cornus*. The photographs were taken of two-year-old plants as grown outdoors in a trial plot in Smithville, Tennessee.

Figure 1:
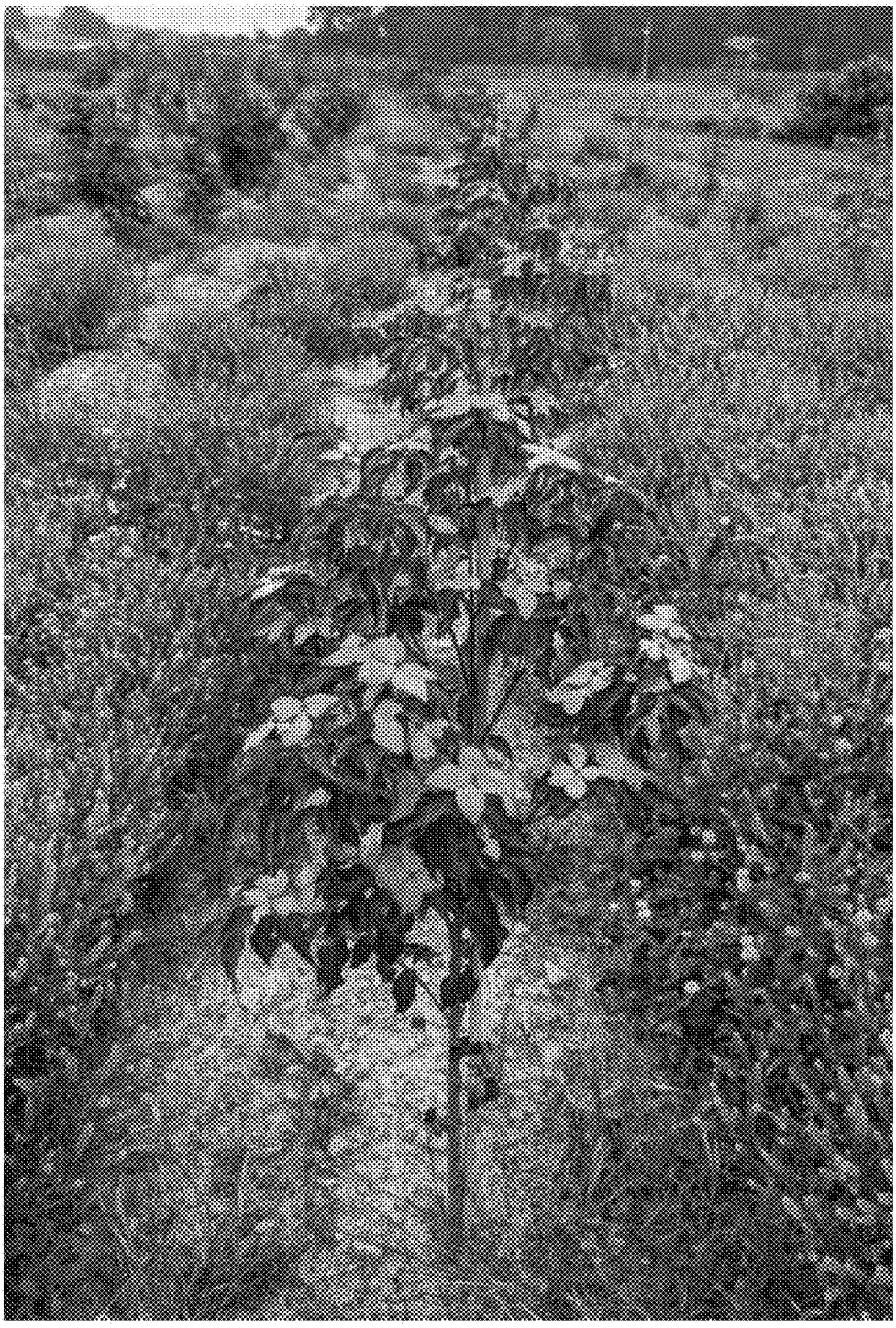

The photograph in FIG. 1 provides a side view of the plant habit of 'Botfire' in bloom.

Figure 2:
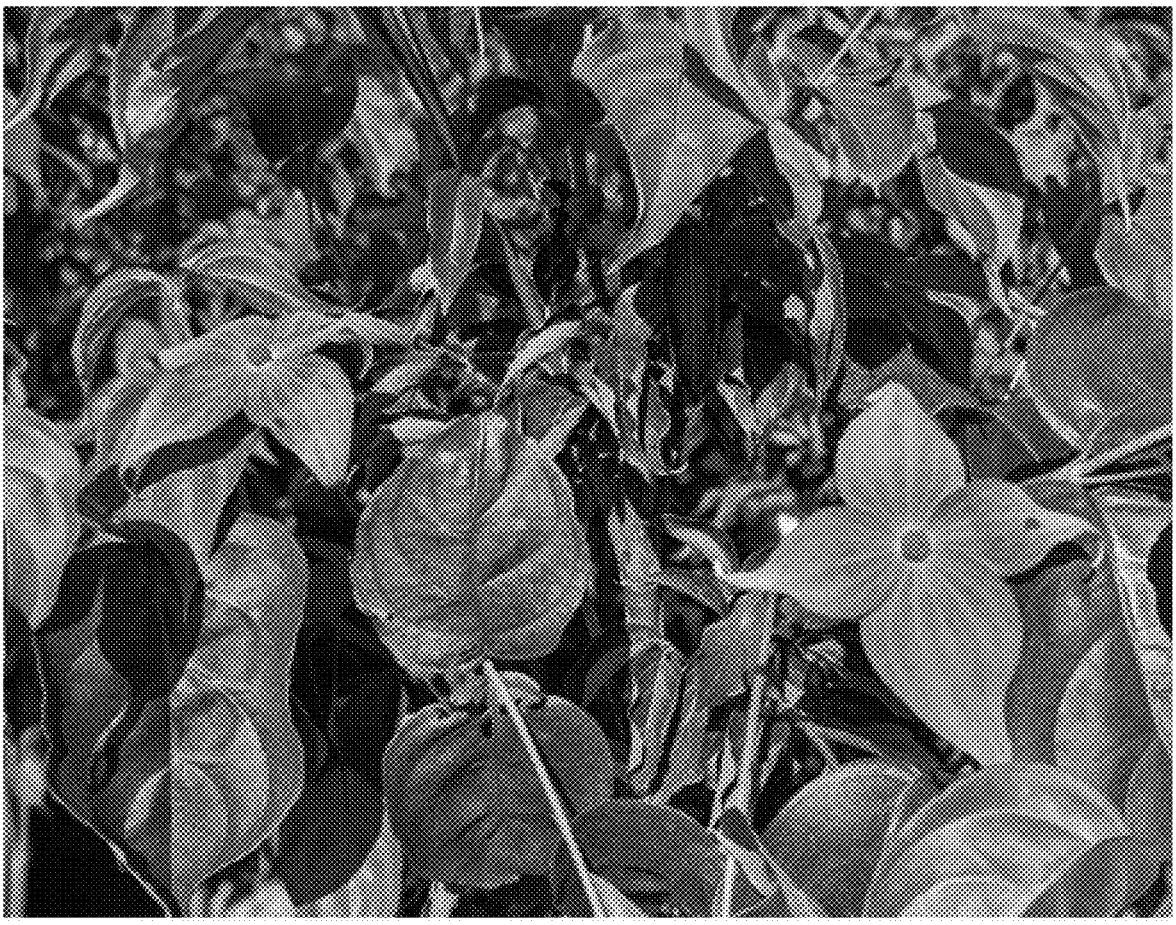

The photograph in FIG. 2 provides a close-up view of the flowers of 'Botfire'.

Figure 3:
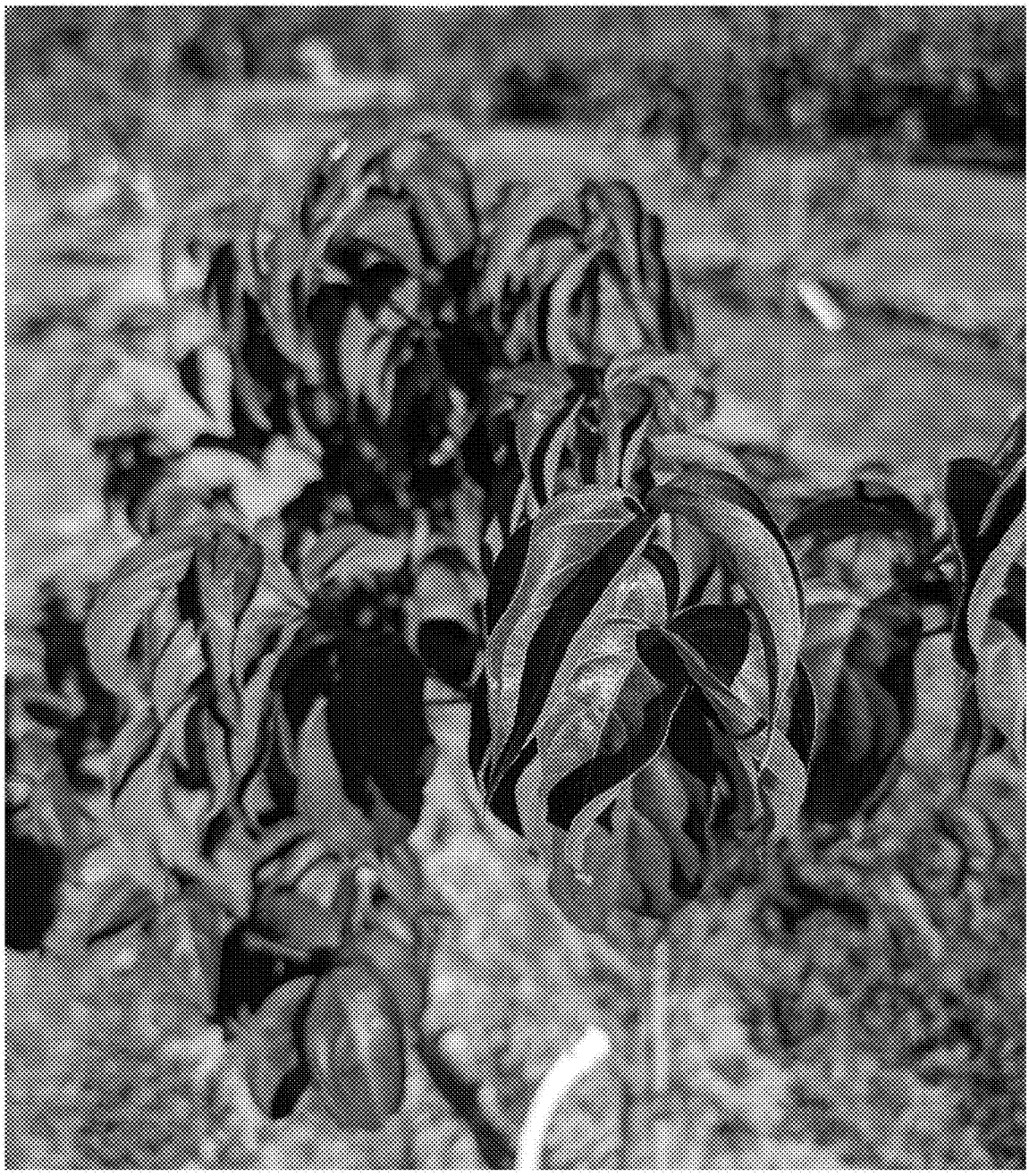

The photograph in FIG. 3 provides a view of the autumn foliage of 'Botfire'.

The colors in the photographs are as close as possible with the photographic and printing technology utilized and the color values cited in the detailed botanical description accurately describe the colors of the new *Cornus.*

DETAILED BOTANICAL DESCRIPTION

The following is a detailed description of two year-old plants of the new *Cornus* as grown in 10-gallon containers in Smithville, Tennessee. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms from March to October in Tennessee.

*Plant type*.—Deciduous shrub.

*Plant habit*.—Upright, sturdy stem, vase-shaped with a rounded top.

*Plant height and spread*.—Reaches up to 9.14 m in height and spread as a mature tree in the landscape and 1.5 m in height and 54 cm in spread in a 10-gallon container.

*Diseases and pests*.—Has shown resistance to dogwood anthracnose (caused by *Discula destructive*) and powdery mildew (caused by *Microsphaera* sp. and *Phyllactinia* sp.), no susceptibility and resistance to pests has been observed.

*Cold hardiness*.—At least in U.S.D.A. Zones 4 to 8.

*Root description*.—Fibrous and fine, 162D in color.

*Propagation*.—Chip budding onto *Cornus kousa* rootstock preferred.

*Root development*.—An average of 2 weeks for root initiation with a young rooted plant produced in an average of 4 weeks.

*Growth rate*.—Typical of the species.

Branch description:

*Branch shape*.—New growth; squared to rounded, mature branches; rounded.

*Branch color*.—New growth; 144A, slightly flushed with 182A, maturing wood; a blend of 165A and 164A, bark and old wood; a blend of 198A and 197A.

*Branch size*.—Main branch; 50 cm in length (from soil to start of lateral branches), 1.5 m in length (total length from soil to end of main branch), lateral branches; up to 33 cm in length and 5 mm in width, tertiary branches; 21 cm in length, 3 mm in diameter.

*Branch surface*.—New growth; smooth, dull, and lightly pubescent with very small hairs NN155D in color, mature stems and bark; glabrous and covered with lenticels less than 0.5 mm in length and 199D in color.

*Internode length*.—An average of 10 cm in length.

*Branching*.—1 main branch, 18 lateral branches, 2 tertiary branches per lateral branch.

Foliage description:

*Leaf shape*.—New leaves; lanceolate, mature leaves; oval to elliptic.

*Leaf division*.—Simple.

*Leaf base*.—Cuneate to oblique.

*Leaf apex*.—Acuminate.

*Leaf fragrance*.—None.

*Leaf venation*.—Pinnate, color upper surface young and mature; 144B with main vein sometimes becomes 162C and then flushed with 183A, lower surface young and mature; 146B.

*Leaf margins*.—Entire and moderately undulate.

*Leaf arrangement*.—Opposite.

*Leaf attachment*.—Petiolate.

*Leaf surface*.—Both surfaces glossy, glabrous.

*Leaf color*.—Upper surface young and mature; 137A, mottled with 144B, main vein sometimes becomes 162C and then flushed with 183A, autumn; a blend of NN137A, 183A, and 184A, veins a blend of 164A and 184C, lower surface young and mature; 146B, autumn; 184C.

*Petioles*.—An average of 4 mm in length and 2 mm in width, surfaces are glabrous, matte, concave, summer color; 146B, sometimes flushed with 182A, autumn color; a blend of 164A and 184C.

*Stipules*.—None observed.

Inflorescence description:

*Inflorescence type*.—Round bracteolate umbel surrounded by showy bracts.

*Inflorescence size*.—An average of 7 mm in diameter and depth, including bracts 7.5 cm in width and 1.5 cm in depth.

*Flower buds*.—Obovate in shape, 137B in color, an average of 2 mm in length and 1.5 mm in width, pubescent surface.

*Flower fragrance*.—None.

*Lastingness of inflorescence*.—3 weeks in mid-summer.

*Flower quantity*.—An average of 60 flowers per inflorescence.

*Flower type*.—Rotate.

*Flower size*.—An average of 2.5 cm in diameter, 1 cm in depth.

*Peduncles*.—Primary an average of 12.5 cm in length to base of inflorescence and 1.5 mm in diameter, very slightly puberulent and dull surface, round in shape with vertical ridges.

*Pedicels*.—None present.

*Bracts* (*showy*).—4, ovate in shape, acuminate apex, cuneate into truncate base, color a blend of 54B and 54C in on upper surface and a blend of 155A and 145C with palmate veins 54C on lower surface, spreading upward, glabrous on both surfaces, an average of 4 cm in length and 2.5 cm in width.

*Bracts* (*imbricate*).—About 30, surrounding base of inflorescence and curled inwards, an average of 1.5 mm in length and 1 mm in width, pubescent on both surfaces, truncate base, broadly acute apex, 137C in color on both surfaces.

*Sepals*.—4, fused, 137B in color on both surfaces, acute apex, truncate base, 1.5 mm in length and 1 mm in width, glabrous and dull on both surfaces.

*Petals*.—4, base fused to top of calyx, spreading, oblong in shape, 2 mm in length and 1 mm in width, margins entire, apex acute, outer and inner surface is glabrous, color of inner and outer surface is 145B.

Reproductive organs: None observed as the true flowers have not opened to date.

Fruit and seed: None observed to date.

It is claimed:

1. A new and distinct cultivar of *Cornus* plant named 'Botfire' as herein illustrated and described.

* * * * *